United States Patent [19]
Falk et al.

[11] Patent Number: 5,674,857
[45] Date of Patent: Oct. 7, 1997

[54] USE OF HYALURONIC ACID TO REPAIR ISCHEMIA REPERFUSION DAMAGE

[75] Inventors: Rudolf Edgar Falk; Samuel Simon Asculai; Ehud Shmuel Klein, all of Toronto, Canada

[73] Assignee: Hyal Pharmaceutical Corporation, Mississauga, Canada

[21] Appl. No.: 200,309

[22] Filed: Feb. 23, 1994

Related U.S. Application Data

[63] Continuation of Ser. No. 838,673, Feb. 21, 1992, abandoned.

[30] Foreign Application Priority Data

Feb. 20, 1992 [CA] Canada .................. 2061567-2

[51] Int. Cl.⁶ .................................................. A61K 31/70
[52] U.S. Cl. ............................................ 514/54; 536/55.1
[58] Field of Search ............................... 519/59; 536/55.1

[56] References Cited

U.S. PATENT DOCUMENTS

| | | | |
|---|---|---|---|
| 4,141,973 | 2/1979 | Balazs | 536/55.1 |
| 4,303,676 | 12/1981 | Balazs | 424/359 |
| 4,582,865 | 4/1986 | Balazs et al. | 524/29 |
| 4,636,524 | 1/1987 | Balazs et al. | 514/781 |
| 4,684,627 | 8/1987 | LeVeen et al. | 514/25 |
| 4,711,780 | 12/1987 | Fahim | 424/145 |
| 4,713,448 | 12/1987 | Balazs et al. | 536/55.1 |
| 4,719,201 | 1/1988 | Foker | 514/23 |
| 4,725,585 | 2/1988 | Wenge et al. | 514/54 |
| 4,736,024 | 4/1988 | Della Valle et al. | 536/55.3 |
| 4,755,544 | 7/1988 | Makino et al. | 524/92 |
| 4,782,046 | 11/1988 | Brown et al. | 536/55.1 |
| 4,784,990 | 11/1988 | Nimrod et al. | 536/55.1 |
| 4,795,741 | 1/1989 | Leshchiner et al. | 514/21 |
| 4,801,619 | 1/1989 | Lindbland | 536/55.1 |
| 4,806,567 | 2/1989 | Ferrari et al. | 514/513 |
| 4,808,576 | 2/1989 | Schultz et al. | 514/59 |
| 4,814,176 | 3/1989 | Makino et al. | 424/457 |
| 4,840,941 | 6/1989 | Ueno et al. | 514/59 |
| 4,851,521 | 7/1989 | della Valle et al. | 536/55.1 |
| 4,931,460 | 6/1990 | Grover et al. | 514/381 |
| 4,937,254 | 6/1990 | Sheffield et al. | 514/40 |
| 4,957,744 | 9/1990 | della Valle et al. | 424/401 |
| 4,965,353 | 10/1990 | della Valle et al. | 536/55.1 |
| 4,968,671 | 11/1990 | Asano et al. | 514/18 |
| 4,970,298 | 11/1990 | Silver et al. | 530/356 |
| 4,988,515 | 1/1991 | Buckberg | 424/529 |
| 5,057,494 | 10/1991 | Sheffield | 514/12 |
| 5,095,027 | 3/1992 | Goldberg et al. | 514/369 |
| 5,095,037 | 3/1992 | Iwamitsu et al. | 514/361 |
| 5,099,012 | 3/1992 | Wu et al. | 536/17.5 |
| 5,166,331 | 11/1992 | Fidia | 536/55.1 |

FOREIGN PATENT DOCUMENTS

| | | |
|---|---|---|
| 15456/88 | 9/1988 | Australia . |
| 14534/88 | 11/1990 | Australia . |
| 17459/88 | 8/1991 | Australia . |
| 1205031 | 5/1986 | Canada . |
| 1240929 | 8/1988 | Canada . |
| 2031880 | 12/1990 | Canada . |
| 769 287 | 3/1957 | European Pat. Off. . |
| 0 138 572 | 4/1985 | European Pat. Off. . |
| 0 179 442 | 4/1986 | European Pat. Off. . |
| 0 197 718 | 10/1986 | European Pat. Off. . |
| 0 208 623 | 1/1987 | European Pat. Off. . |
| 0 216 453 | 4/1987 | European Pat. Off. . |
| 0 244 178 | 4/1987 | European Pat. Off. . |
| 0 224 987 | 6/1987 | European Pat. Off. . |
| 0 240 098 | 10/1987 | European Pat. Off. . |
| 0 265 116 | 4/1988 | European Pat. Off. . |
| 0 270 317 | 6/1988 | European Pat. Off. . |
| 0 285 357 | 10/1988 | European Pat. Off. . |
| 0 287 210 | 10/1988 | European Pat. Off. . |
| 0 295 092 | 12/1988 | European Pat. Off. . |
| 0 312 208 | 4/1989 | European Pat. Off. . |
| 0 341 745 | 5/1989 | European Pat. Off. . |
| 1287041 | of 0000 | Japan . |
| 61-000017 | 1/1986 | Japan . |
| 62-201825 | of 1987 | Japan . |
| WO 88/07060 | 9/1988 | WIPO . |
| WO 89/07932 | 9/1989 | WIPO . |
| Wo 91/04058 | 4/1991 | WIPO . |
| WO 91/15215 | 10/1991 | WIPO . |

OTHER PUBLICATIONS

U.S. application No. 07/338,106, Falk, Filed Apr. 4, 1989.
Sandra Blakeslee, "Solid cores of tumors keeping out best drugs", Jul. 8, 1989 edition of the Globe and Mail, Toronto, Ontario, p. D4.
Pam Harrison, "Toxic drug tamed by still potent" *Ontario Medicine*, vol. 8, No. 16 dated Aug. 21, 1989, p. 1.
The Merck Index Eleventh Edition, Centennial Edition, Hyaluronic Acid formulation, pp. 751 and 752.
Alan R. Liss, Inc., Modulation of Immunity in Cancer Patients by Prostaglandin Antagonists, *Immunity to Cancer II*.
Goodwin, J.S. Prostaglandin E and Cancer Growth Potential for Immunotherapy with Prostaglandin Synthesis Inhibitors, *Augmentive Agents in Cancer Therapy*, Raven Press, New York, (1981).
Dr. Samuel Asculai, "Inactivation of Herpes Simplex Viruses by Nonionic Surfactants", *Antimicrobial Agents and Chemotherapy*, Apr. 1978, pp. 686–690.
Chemical Abstracts, vol. 76, No. 10; W. E. Sneader; "Possible Mechanism for action of DMSO on Percutaneous absorption", J. Pharm. Pharmcol., 1971, 23 (Supp).

*Primary Examiner*—Elli Peselev
*Attorney, Agent, or Firm*—Ivor M. Hughes; Neil H. Hughes; Marcelo K. Sarkis

[57] ABSTRACT

A pharmaceutical composition comprising an effective non-toxic amount of hyaluronic acid (HA) and or salts thereof and/or homologues, analogues, derivatives, complexes, esters, fragments and units of HA in association with a suitable diluent or pharmaceutically acceptable carrier for use in treating ischemia damage in tissue.

18 Claims, 3 Drawing Sheets

5,674,857

USE OF HYALURONIC ACID TO REPAIR ISCHEMIA REPERFUSION DAMAGE

This application is a continuation of application Ser. No. 07/838,673, filed Feb. 21, 1992, now abandoned.

FIELD OF INVENTION

This invention relates to repair through reperfusion of ischemia damage to tissue particularly internal organs and most particularly to the liver, heart, and kidneys and formulations for use to repair through reperfusion such ischemia damage and methods of treating such conditions.

BACKGROUND OF THE INVENTION

U.S. Pat. No. 4,801,619 relates to hyaluronic acid administered intra-articularly having a molecular weight of about $3 \times 10^6$ dalton more, which is prone to decrease the proteoglycan content of synovial fluid to almost normal levels. According to this patent, this indicates a positive effect on the proteoglycan metabolism of a joint. According to the Patent this is applicable both to inflammatory conditions and to degeneration caused by treatment with symptomatics, such as corticosteroid preparations. It is thus clear that a sufficiently high molecular weight of the hyaluronic acid is alleged to counteract side effects that might be caused by corticosteroids or other symptomatics producing similar effects. When corticosteroids are applied, the amount of hyaluronic acid in the synovial cavity will according to the Patent increase substantially and according to the inventors their hyaluronic acid preparations have a very positive effect on such clinical symptoms as pain, swelling and lameness.

The patent states that the objectives of the invention are attained by intra-articular administration of an effective amount of hyaluronic acid with a mean molecular weight exceeding $3 \times 10^6$ dalton, preferably exceeding $4 \times 10^6$ dalton; usually the molecular weight will not exceed $7 \times 10^6$ dalton. The dosage of hyaluronic acid administered is stated to be preferably within the range of 5 mg–80 mg. The amount of solution given at each administration is generally less than 60 ml, e.g. less that 20 ml, of an aqueous solution of the acid or its salt. It is convenient to administer the acid dissolved in water (<2% w/w, buffered to physiological pH), for instance in the form of a water-soluble sodium salt. The exact amount will depend on the particular joint to be treated.

The Merck Index specifies that hyaluronic acid has a molecular weight within the range pf 50,000 to $8 \times 10^6$ depending on source, methods of preparation and methods of determination. The Merck Publication teaches hyaluronic acid as a surgical aid (ophthalmological).

U.S. Pat. No. 4,808,576 purports to teach that hyaluronic acid, an agent well known to reduce the sequelae of trauma in mammalian joint tissue when applied directly to the traumatized tissue, will be carried to such traumatized tissue by the mammal's natural processes if applied at a site remote from the traumatized tissue. Thus hyaluronic acid in any therapeutically acceptable form can, according to the Patent, be administered by the typical remote routes including intravenous, intramuscular, subcutaneous and topical.

This, the patent alleges, makes the utilization of hyaluronic acid much more convenient and attractive. For instance the treatment of arthritis in horse or human joints with hyaluronic acid according to the patent no longer requires more difficult intra articular injections.

U.S. Pat. No. 4,725,585 relates to a method of enhancing or regulating the host defence of a mammal, said method comprising administering to a mammal a therapeutically effective amount of hyaluronic acid.

At column 1 lines 43–46, the patent provides that the invention was based on the unexpected discovery that administration of hyaluronic acid to mammals results in a considerable increase in the defence.

We have now discovered that hyaluronic acid and its salts and other forms are useful in repairing ischemia reperfusion damage in tissue particularly internal organs and most particularly the liver.

SUMMARY OF THE INVENTION

According to one aspect of the invention, a formulation for administration to a mammal is provided comprising an amount of hyaluronic acid and or salts thereof and/or homologues, analogues, derivatives, complexes, esters, fragments and sub units of hyaluronic acid effective to prevent or repair ischemia reperfusion damage in tissue particularly internal organs for example the liver, together with a pharmaceutical carrier.

The hyaluronic acid in a carrier may be administered intravenously, by infusion or any other suitable method and may be administered up to about 7 gm per 70 kg person per day. While reduced amounts of hyaluronic acid may be delivered in the carrier it is preferable that the least amount of hyaluronic acid be in the range of about 300 mg/70 kg person per day.

According to another aspect of the invention, a method of repairing ischemia reperfusion damage in tissue, particularly internal organs, and more particularly the liver, is provided comprising administering to the mammal a therapeutically effective amount of hyaluronic acid and or salts thereof and/or homologues, analogues, derivatives, complexes, esters, fragments and sub units of hyaluronic acid in a suitable carrier. Because hyaluronic acid targets the damaged tissue and facilitates its own penetration through the tissue at the site to be treated through the cell membranes into the individual cells to be treated, it rapidly arrives at the site after introduction, for example, by intravenous methods and repairs the ischemia reperfusion damage in the tissue, for example the liver, or prevents or minimizes such damage (as for example in transplants such as the liver, heart, lungs, and kidneys).

The formulation can be administered among other methods, intravenously, intra-arterially, intraperitoneally, intrapleurally, transdermally, on the skin, or by direct injection (for example into the liver). In one embodiment there is provided a pharmaceutical composition comprising in a pharmaceutically acceptable form for treating ischemia, an effective non-toxic amount of hyaluronic acid and or salts thereof, homologues, analogues, derivatives, complexes, esters, fragments and sub units of hyaluronic acid for use in treating ischemia damage in tissue in association with a suitable diluent or pharmaceutically acceptable carrier.

One form of hyaluronic acid and/or salts thereof (for example sodium salt) and homologues, analogues, derivatives, complexes, esters, fragments and sub units of hyaluronic acid, preferably hyaluronic acid and salts and thereof suitable for use with Applicant's invention is a fraction suppled by Hyal Pharmaceuticals Limited. One such fraction is a 15 ml vial of Sodium hyaluronate 20 mg/ml (300 mg/vial-Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in Type 1 borosilicate g vial closed by a butyl stopper which does not react with the contents of the vial.

The fraction of hyaluronic acid and/or salts thereof (for example sodium salt) and homologues, analogues, derivatives, complexes, esters, fragments and sub units of hyaluronic acid, preferably hyaluronic acid and salts and thereof may comprise hyaluronic acid and/or salts thereof having the following characteristics:

a purified, substantially pyrogen-free fraction of hyaluronic acid obtained from a natural source having at least one characteristic selected from the group consisting of the following:

(i) a molecular weight within the range of 150,000–700,000;

(ii) less than about 1.25% sulphated mucopolysaccharides on a total weight basis;

(iii) less than about 0.6% protein on a total weight basis;

(iv) less than about 150 ppm iron on a total weight basis;

(v) less than about 15 ppm lead on a total weight basis;

(vi) less than 0.0025% glucosamine;

(vii) less than 0.025% glucuronic acid;

(viii) less than 0.025% N-acetylglucosamine;

(ix) less than 0.0025% amino acids;

(x) a UV extinction coefficient at 257 nm of less than about 0.275;

(xi) a UV extinction coefficient at 280 nm of less than about 0.25; and (xii) a pH within the range of 7.3–7.9.

Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:

(i) less than about 1% sulphated mucopolysaccharides on a total weight basis;

(ii) less than about 0.4% protein on a total weight basis;

(iii) less than about 100 ppm iron on a total weight basis;

(iv) less than about 10 ppm lead on a total weight basis;

(v) less than 0.00166% glucosamine;

(vi) less than 0.0166% glucuronic acid;

(vii) less than 0.0166% N-acetylglucosamine;

(viii) less than 0.00166% amino acids;

(ix) a UV extinction coefficient at 257 nm of less than about 0.23;

(x) a UV extinction coefficient at 280 nm of less than about 0.19; and (xi) a pH within the range of 7.5–7.7.

Other forms of hyaluronic acid and/or its salts, and homologues, derivatives, complexes, esters, fragments and sub units hyaluronic acid may be chosen from other suppliers, for example those described in the prior art documents previously referred to. In addition Applicants have successfully employed sodium hyaluronate produced and supplied by LifeCore™ Biomedical, Inc. having the following specifications

| Characteristics | Specification |
| --- | --- |
| Appearance | White to cream colored particles |
| Odor | No perceptible Odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, Maximum ppm | |
| As Cd Cr Co  Cu  Fe  Pb  Hg  Ni
2.0 5.0 5.0 10.0 10.0 25.0 10.0 10.0 5.0 | |
| Microbial Bioburden | None Observed |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 $cm^3/g$., and preferably greater than about 2000 $cm^3/g$.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiolocal buffer of less than $-11 \times 10^3$ degree-$cm^2$/mole (of disaccharide) measure at 220 nanometers;

(f) no significant cellular infiltration of the vitreaous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being;

(g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

According to yet another aspect of the invention, Alanine Aminotransferase production in damaged tissue, for example the liver is reduced by the administration of, for example hyaluronic acid and/or salts thereof in association with a suitable diluent or pharmaceutically acceptable carrier.

The following examples are offered to illustrate Applicants' invention but in no way limit the scope of the invention.

Applicants believe that Drug uptake is affected by cellular damage associated with tissue malperfusion. The glycosaminoglycan, Hyaluronic Acid (HA) has been shown to affect cellular membrane activity. To assess its potential effect upon drug uptake we did the following studies. We studied the effect of HA on tritiated 5-Fluorouracil ($^3$H-5-FU) uptake by acute and chronic malperfused rat liver tissue using 2 models.

EXAMPLE 1

Ischemia/Reperfusion

Two groups of rats (A,B) were subjected to 30 minute liver ischemia followed by a period of reperfusion. Two sham groups (C, D) served as controls. Two additional groups (E, F) underwent a 'once-through' liver perfusion in order to quantitate tissue bound drug. All groups received intravenous $^3$H-5-Flourouracil (a radioactive tracer) ($^3$H-5-FU) at the end of the reperfusion period. Groups A, C, and F received in addition intravenous (HA) Hyaluronic Acid (15 mg/kg).

Samples of liver tissue were processed and counted for radioactivity. The groups treated with HA showed a significantly higher (10%, p<0.05 ANOVA) uptake of $^3$H-5-Fu than in the untreated groups. Following 'once through' perfusion the difference between the groups persists.

EXAMPLE 2

Figure 1:
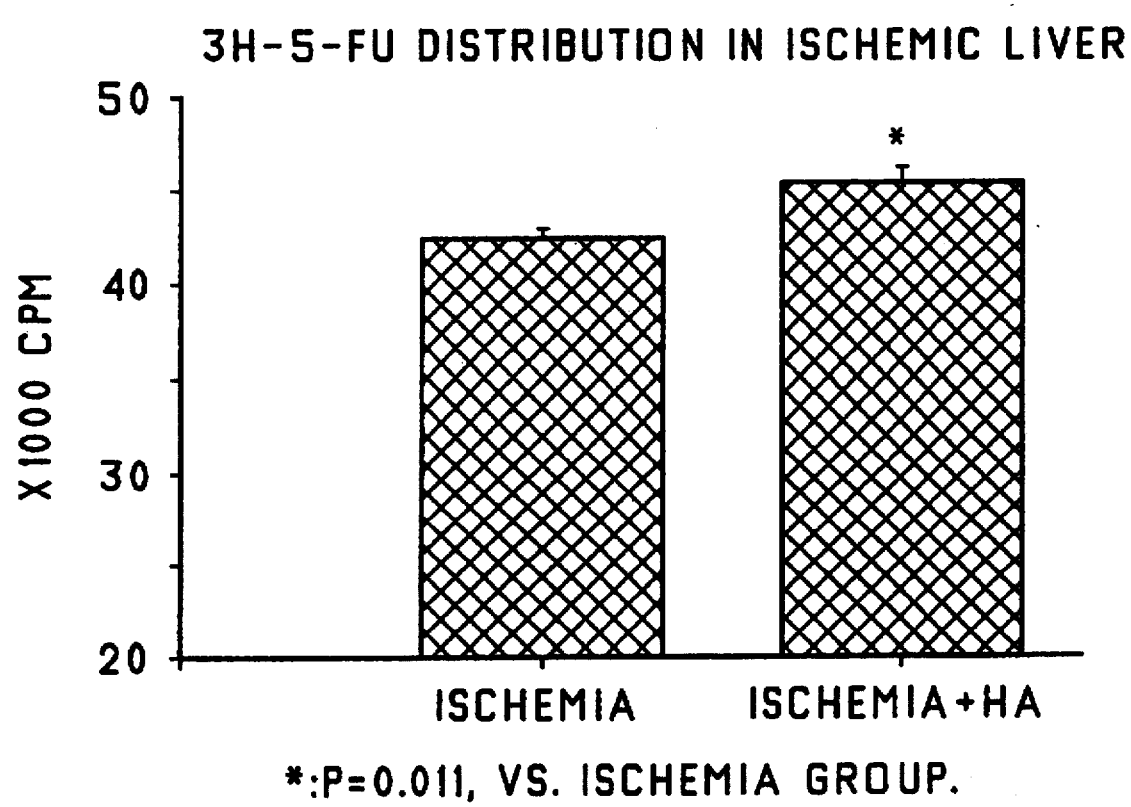
FIG. 1 is a chart showing the $^3$H-5Fu-Distribution is Ischemic Liver with hyaluronic acid and without hyaluronic acid.
Figure 2:
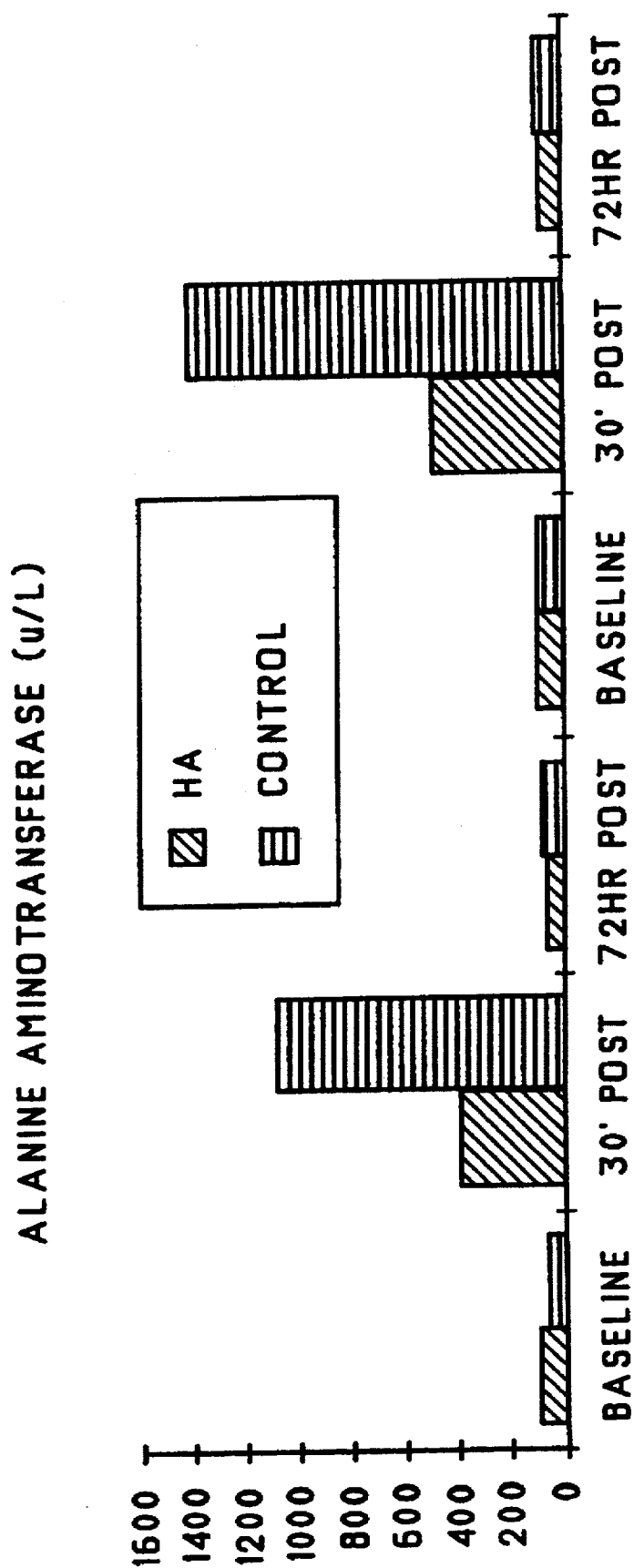
FIG. 2 is a chart showing Alanine Aminotransferase release in damaged liver, one group with hyaluronic acid and one group without hyaluronic acid given.

Liver Tumor (see FIG. 1)

Two groups of rats with liver-implanted mammary carcinoma received intravenous $^3$H-5-FU. One of the groups received intravenous HA as well. Samples of tumour tissue were processed and counted for radioactivity. The uptake $^3$H-5-FU by tumour tissue was higher (40%, p<0.05 ANOVA) in the HA treated group compared to the untreated group.

The results in examples 1 and 2 teach that HA is involved in the observed enhancement of $^3$H-5-FU uptake by ischemia/reperfused rat liver and by rat liver tumour. It has been previously suggested that the tissue injury or neoplasia may alter local HA production. Applicants have now found that exogenously given HA preferentially targets such tissues. The following data is offered.

| ISCHEMIA | | ISCHEMIA + HA | |
|---|---|---|---|
| mean | sem | mean | sem |
| 42952 | 940 | 48277 | 871 |
| 43500 | 847 | 49130 | 771 |
| 44261 | 776 | 41431 | 1131 |
| 44692 | 648 | 46140 | 863 |
| 42727 | 324 | 43189 | 950 |

-continued

| ISCHEMIA | | ISCHEMIA + HA | |
|---|---|---|---|
| mean | sem | mean | sem |
| 41288 | 1793 | 43911 | 692 |
| 39545 | 595 | 45753 | 614 |
| 40544 | 280 | 46919 | 299 |
| 42871 | 1001 | 43776 | 535 |
| 42487 | | 45392 | |
| 569 | | 839 | |

The following additional data is also offered.

| | SUM SQUARES | DEG FREEDOM | MEAN SQUARE |
|---|---|---|---|
| TREATMENT | 3.81E+07 | 1 | 3.81E+07 |
| ERROR | 7.40E+07 | 16 | 4622828 |
| TOTAL | 1.12E+08 | | |
| F-TEST RATIO = | 8.232406 | | |
| SIGNIFICANCE = | 0.0111 | | |

| TREATMENT | MEAN | STANDARD ERROR | NUMBER OF OBSERVATIONS |
|---|---|---|---|
| VAR - 1 | 42483.67 | 568.8718 | 9 |
| VAR - 2 | 45391.78 | 838.8565 | 9 |

| TREATMENT | MEAN | DUNCAN'S MULTIPLE-RANGE TEST |
|---|---|---|
| GROUP 1 | 42483.67 | |
| GROUP 2 | 45391.78 | |

STANDARD ERROR OF TREATMENT MEANS = 716.6921

| TREATMENT VS. | TREATMENT | DIFFERENCE | SIG. 0.5 | SIG .01 |
|---|---|---|---|---|
| GROUP 1 | GROUP 2 | 2908.109 | * | — |

| TREATMENT | MEANS | NEWMAN-KEULS' MULTIPLE-RANGE TEST |
|---|---|---|
| GROUP 1 | 42483.67 | |
| GROUP 2 | 45391.78 | |

STANDARD ERROR OF TREATMENT MEANS = 716.6921

| TREATMENT VS. | TREATMENT | DIFFERENCE | SIG. 0.5 | SIG .01 |
|---|---|---|---|---|
| GROUP 1 | GROUP 2 | 2908.109 | * | — |

| TREATMENT | MEAN | DUNNETT'S MULTIPLE-RANGE TEST |
|---|---|---|
| GROUP 1 | 42483.67 | |
| GROUP 2 | 45391.78 | |

STANDARD ERROR OF TREATMENT MEANS = 1013.556

| TREATMENT VS. | TREATMENT | DIFFERENCE | SIG. 0.5 | SIG .01 |
|---|---|---|---|---|
| GROUP 1 | GROUP 2 | 2908.109 | * | — |

| -continued | | |
|---|---|---|
| TREATMENT | MEAN | LEAST SIGNIFICANT DIFFERENCE MULTIPLE-RANGE TEST |
| GROUP 1 | 42483.67 | |
| GROUP 2 | 45391.78 | |

STANDARD ERROR OF TREATMENT MEANS = 716.6921

| TREATMENT VS. | TREATMENT | DIFFERENCE | SIG .05 |
|---|---|---|---|
| GROUP 1 | GROUP 2 | 2908.109 | * |

EXAMPLE 3

Alanine Aminotransferase (ALT) is an enzyme released by the liver when the liver is damaged or when experiencing ischemia. The lower the level of released ALT, the lower the level of damage. Two groups of rats underwent liver ischemia by clamping off the hepatic artery to the liver for 30 minutes followed by a period of reperfusion. One group was given intravenously a control injection whereas the other group was given HA (Sodium hyaluronate) intravenously. Both groups were measured for Alanine Aminotransferase levels. The group which received HA demonstrated significantly lower levels of Alanine Aminotransferase enzyme in the blood stream compared to the control groups.

ALT (Alanine Aminotransferase) Measurement in Ischemia/Reperfusion Rats (Blood Stream). Absolute value Expressed as percentage of baseline

| | rat# | Baseline | 30' | 72 hrs | Baseline | 30' | 72 hrs |
|---|---|---|---|---|---|---|---|
| Group 1 | | | | | | | |
| +HA | 1 | 80 | 592 | 137 | 740 | 171 | |
| | 3 | 173 | 518 | | | 299 | |
| | 5 | 80 | 264 | 47 | 330 | 59 | |
| | 7 | 89 | 310 | 40 | 348 | 45 | |
| | 9 | 59 | 484 | 43 | 820 | 73 | |
| | 11 | 87 | 323 | | 371 | | |
| mean | | 94.67 | 415.75 | 66.75 | 484.89 | 86.96 | |
| sed | | 16.26 | 54.46 | 23.46 | 94.44 | 28.67 | |
| Group 2 | | | | | | | |
| | 2 | 86 | 1420 | 84 | 1651 | 98 | |
| | 4 | 90 | 603 | 70 | 670 | 78 | |
| | 6 | 57 | 361 | | 633 | | |
| | 8 | 78 | 2010 | 92 | 2577 | 118 | |
| | 10 | 64 | 1040 | | 1625 | | |
| mean | | 75 | 1086.6 | 82 | 1431.28 | 97.80 | |
| sed | | 6.32 | 293.80 | 6.43 | 361.57 | 11.60 | |

(SEE FIG. 2)

Figure 3:
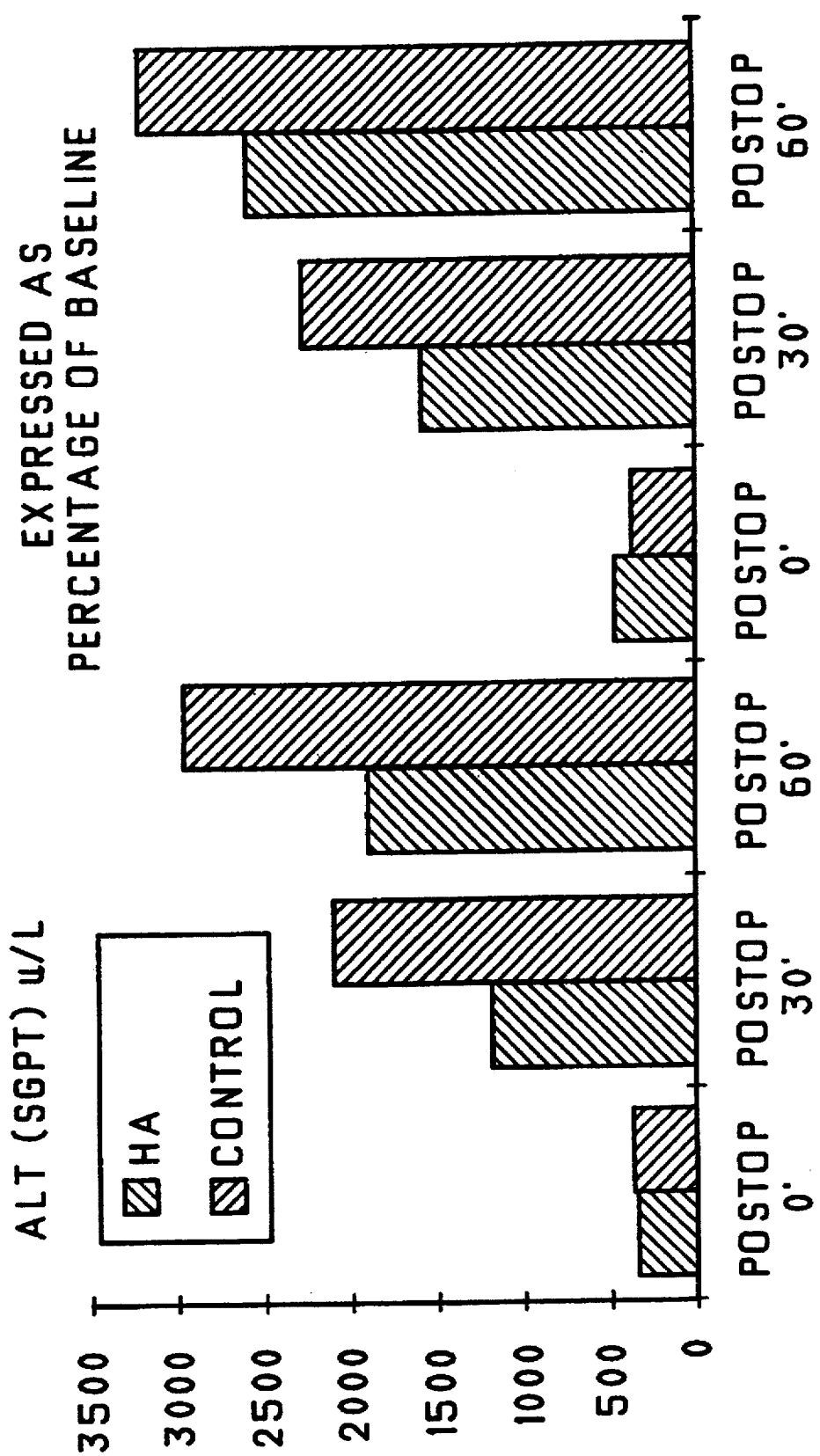
FIG. 3 is a chart showing the Alanine transferase in Ischemic Rats, Bloodstream, one group given hyaluronic acid and the other group not given hyaluronic acid.

Further test data is set out below:
(See FIG. 3)

Alanine Transferase Measurement in Ischemia Rats [Blood Stream];

| RAT# | PREOP | POSTOP 0' | POSTOP 30' | POSTOP 60' | POP 0'% | POP 30'% | POP 60'% |
|---|---|---|---|---|---|---|---|
| 1 | 67 | 229 | 1289 | 2030 | 342 | 1924 | 3030 |
| 2 | 73 | 279 | 1220 | 2120 | 382 | 1671 | 2904 |
| 3 | 76 | 890 | 1310 | 2020 | 1171 | 1724 | 2658 |
| 4 | 74 | 395 | 1070 | 1160 | 534 | 1446 | 1568 |
| 5 | 78 | 158 | 1080 | 1390 | 203 | 1385 | 1782 |

| | | | -continued | | | | |
|---|---|---|---|---|---|---|---|
| 6 | 68 | 215 | 1170 | 2840 | 316 | 1721 | 4176 |
| 7 | 81 | 272 | 1140 | 1670 | 336 | 1407 | 2062 |
| MEAN | | 348.29 | 1182.71 | 1890.00 | 469.05 | 1611.05 | 2597.10 |
| SEM | | 101.99 | 38.78 | 225.04 | 132.59 | 82.69 | 364.79 |
| 8 | 98 | 478 | 1860 | 2940 | 488 | 1898 | 3000 |
| 9 | 83 | 190 | 2020 | 2600 | 229 | 2434 | 3133 |
| 10 | 89 | 436 | 2930 | 3400 | 490 | 3292 | 3820 |
| 11 | 105 | 590 | 1930 | 2600 | 562 | 1838 | 2476 |
| 12 | 88 | 277 | 2020 | 3400 | 315 | 2295 | 3864 |
| 13 | 91 | 220 | 2170 | 3710 | 242 | 2385 | 4077 |
| 14 | 98 | 343 | 1730 | 1940 | 350 | 1765 | 1980 |
| MEAN | 83.5 | 362.00 | 2094.29 | 2941.43 | 382.14 | 2272.47 | 3192.73 |
| SEM | | 59.69 | 160.71 | 249.85 | 53.71 | 215.06 | 318.48 |

| MEAN COMPARISON | | |
|---|---|---|
| | HA | CONTROL |
| postop 0' | 348 | 362 |
| postop 30' | 1183 | 2094 |
| postop 60' | 1890 | 2941 |
| postop 0' | 469 | 382 |
| postop 30' | 1611 | 2272 |
| postop 60' | 2597 | 3193 |

As many changes can be made to the preferred embodiments of the invention without departing from the scope of the invention; it is intended that all material herein be treated as illustrative of the invention and not in a limiting sense.

The embodiments of the invention in which an exclusive property or privilege is claimed are as follows:

1. A method of treating ischemia damage in tissue in a person comprising administering to such person suffering from ischemia damage, an effective dosage amount of a pharmaceutical composition in a pharmaceutically acceptable intravenous form comprising an effective non-toxic amount, and pharmaceutically acceptable form, of a form of hyaluronic acid selected from the group consisting of hyaluronic acid and pharmaceutically acceptable salts thereof for treating ischemia damage in tissue in such person, in association with a suitable diluent or pharmaceutically acceptable carrier, and wherein the intravenous form is in a dosage form suitable for administration to such person and of a purity suitable for intravenous administration to such person.

2. A method of treating ischemia damage in tissue in a person comprising administering to such person suffering from ischemia damage, an effective dosage amount of a pharmaceutical composition in a pharmaceutically acceptable injectable form comprising an effective non-toxic amount of a form of hyaluronic acid selected from the group consisting of hyaluronic acid and pharmaceutically acceptable salts thereof for treating ischemia damage in tissue in such person in association with a suitable diluent or pharmaceutically acceptable carrier, and wherein the injectable form is in a dosage form suitable for administration to such person and of a purity suitable for injectable administration to such person.

3. The method of claim 1 wherein the amount of the non-toxic and pharmaceutically acceptable form of the form of hyaluronic acid administered is between about 300 mg and about 7 grams/70 kg person.

4. The method of claim 2 wherein the amount of non-toxic and pharmaceutically acceptable form of the form of hyaluronic acid administered is between about 300 mg and about 7 grams/70 kg person.

5. The method of claim 3 wherein the form of hyaluronic acid is sodium hyaluronate.

6. The method of claim 2, 3, 4, or 5 wherein the tissue is selected from the group consisting of the liver, the kidneys, the lungs and the heart.

7. The method of claim 3 or 4 wherein the molecular weight of the form of hyaluronic acid is less than 750,000 daltons.

8. The method of claim 2 or 4 wherein the composition is used for treating ischemia damage in tissue due to transplantation of internal organs.

9. The method of claim 5 wherein the composition is used for treating ischemia damage in tissue due to transplantation of internal organs.

10. The method of claim 5 wherein the composition is used for treating ischemia damage in tissue during transplantation of tissue selected from the group consisting of the liver, kidney or kidneys, the heart and lungs.

11. The method of claim 10 wherein the molecular weight of the form of hyaluronic acid is less than 750,000 daltons.

12. The method of claim 11 wherein the composition is administered just prior to, during, or just after transplantation of the tissue.

13. A method of reducing Alanine Aminotransferase enzyme production by the liver in a person when damaged by, or is experiencing, ischemia, comprising administering to such person a formulation in a pharmaceutically acceptable form, comprising an effective non-toxic amount of a form of hyaluronic acid selected from the group consisting of hyaluronic acid and pharmaceutically acceptable salts thereof for reducing Alanine Aminotransferase enzyme production by the liver when damaged by, or is experiencing, ischemia, in association with a suitable diluent or pharmaceutically acceptable carrier, and wherein the form is in a dosage form suitable for administration to such person and of a purity suitable for administration to such person.

14. The method of claim 13 wherein the amount of the form of hyaluronic acid is from about 300 mg to about 7 grams/70 kg person.

15. The method of claim 4 wherein the form of hyaluronic acid is sodium hyaluronate.

16. The method of claim 15 wherein the form of hyaluronic acid is sodium hyaluronate having a molecular weight less than 750,000 daltons.

17. The method of claim 14 wherein the molecular weight of the form of hyaluronic acid is less than 750,000 daltons and the form of hyaluronic acid is sodium hyaluronate and the pharmaceutically acceptable form of the formulation is for intravenous or injectable administration.

18. The method of claim 4 or 5 wherein the composition is used for treating ischemia damage in tissue due to the transplantation of the lungs.

* * * * *